United States Patent
Senapathy et al.

(10) Patent No.: US 6,368,834 B1
(45) Date of Patent: Apr. 9, 2002

(54) PCR GENOME WALKING WITH SYNTHETIC PRIMER

(75) Inventors: Periannan Senapathy, Madison; Chris Scherrer, Rio, both of WI (US)

(73) Assignee: Genome Technologies, LLC, Madison, WI (US)

( * ) Notice: Subject to any disclaimer, the term of this patent is extended or adjusted under 35 U.S.C. 154(b) by 0 days.

(21) Appl. No.: 09/417,743

(22) Filed: Oct. 14, 1999

Related U.S. Application Data

(60) Provisional application No. 60/127,890, filed on Apr. 6, 1999.

(51) Int. Cl.[7] .......................... C12Q 1/68; C12P 19/34; C07H 21/02; C07H 21/04
(52) U.S. Cl. ...................... 435/91.1; 435/6; 435/91.2; 536/22.1; 536/24.1
(58) Field of Search ............... 536/22.1, 24.2; 435/91.2, 91.1, 6

(56) References Cited

U.S. PATENT DOCUMENTS

| | | | |
|---|---|---|---|
| 4,683,195 A | | 7/1987 | Mullis et al. ................. 435/6 |
| 4,683,202 A | | 7/1987 | Mullis et al. ................. 435/91 |
| 5,516,663 A | * | 5/1996 | Backman et al. ........... 435/91.2 |
| 5,817,797 A | * | 10/1998 | Mitchell et al. ............. 435/6 |
| 6,180,338 B1 | * | 1/2001 | Adams et al. ............... 435/6 |

FOREIGN PATENT DOCUMENTS

| | | | | |
|---|---|---|---|---|
| EP | 0 645 449 A1 | 9/1994 | ........... | C12N/15/10 |
| FR | 2 678 639 | 1/1993 | ............ | C12Q/1/68 |
| WO | WO 92/13110 | 8/1992 | ............ | C12Q/1/68 |
| WO | WO 98/02575 | 1/1998 | ............ | C12Q/1/68 |

OTHER PUBLICATIONS

Landegren et al. A ligase–mediated gene detection technique, Science, vol. 241, pp. 1077–1080, 1988.*
Kalman et al., Polymerase chain reaction (PCR) amplification with a single specific primer, *Biochemical and Biophysical Research Communications*, (1990) vol. 167, No. 2, pp. 504–506.
Shyamala et al., Genome walking by single–specific–primer polymerase chain reaction: SSP–PCR, *Gene*, (1989) 84:1–8.
Troutt et al., Ligation–anchored PCR: A simple amplification technique with single–sided specificity, *Proc. Natl. Acad. Sci. USA*, (1992), vol. 89, pp. 9823–9825.

* cited by examiner

*Primary Examiner*—W. Gary Jones
*Assistant Examiner*—Joyce Tung
(74) *Attorney, Agent, or Firm*—Joseph T. Leone, Esq.; DeWitt Ross & Stevens S.C.

(57) ABSTRACT

Disclosed is a method wherein an unknown DNA sequence 3' to a known DNA sequence is amplified specifically in a first round of PCR using a 5'-blocked primer which hybridizes to the known portion of the DNA sequence. The resultant population of complementary strands to the unknown region is melted to yield single-stranded DNA molecules which are complementary to the unknown DNA sequence, but having a known 5' terminal sequence which is blocked to further reaction. The single-stranded DNA molecules are coupled at their 3' termini to an arbitrary, 3'-blocked synthetic primer of known sequence to yield single-stranded DNA target molecules having a known sequence at both the 5' and 3' termini and an unknown sequence therebetween. Amplification of the DNA target molecules, using primers complementary to the known 5' and 3' termini, causes specific amplification of the unknown DNA between the 5' and 3' termini of the DNA target molecules. The amplified DNA target molecules can be sequenced or otherwise manipulated using standard methods.

12 Claims, 3 Drawing Sheets

Exponential Doubling of Double-Stranded DNA

PCR GENOME WALKING WITH SYNTHETIC PRIMER

Priority is claimed to provisional application Ser. No. 60/127,890, filed Apr. 6, 1999.

FIELD OF THE INVENTION

The invention is directed to a method which specifically amplifies a target nucleic acid region of unknown nucleotide sequence which is disposed downstream from (that is, in the 3' direction from) a portion of the nucleic acid target region having a known nucleotide sequence.

DESCRIPTION OF THE PRIOR ART

The polymerase chain reaction (PCR) enables amplification of a nucleic acid sequence (i.e., deoxyribonucleic acid (DNA) or ribonucleic acid (RNA)) which lies between two regions of known nucleotide sequence. See Mullis et al., U.S. Pat. Nos. 4,683,202 and 4,683,195, the teaching of which is incorporated herein by reference. Oligonucleotides complementary to the known 5' and 3' sequences flanking the unknown portion of the target nucleic acid serve as "primers" in the PCR procedure. In the PCR, double-stranded target nucleic acid is first melted to separate the two strands. The oligonucleotide primers complementary to the known 5' and 3' portions of the segment which is desired to be amplified are then annealed to the target (or "template") nucleic acid. The portions of the nucleic acid target where the primers anneal serve as starting points for the synthesis of new complementary nucleic acid strands. This process utilizes an added DNA or RNA polymerase, most often Taq DNA polymerase, although other DNA polymerases are known. The enzymatic synthesis of the complementary nucleic acid strands is known as "primer extension." The orientation of the 5' and 3' primers with respect to one another is such that the 5' to 3' extension product from each primer contains, when extended far enough, the sequence which is complementary to the other primer. Thus, each newly synthesized nucleic acid strand becomes a template for synthesis of yet another nucleic acid strand beginning with the opposite primer. Repeated cycles of melting, annealing of primers, and primer extension lead to a (near) doubling of nucleic acid strands with each cycle. Each new strand contains the sequence of the target nucleic acid beginning with the sequence of the first primer and ending with the sequence of the second primer.

A key and inescapable requirement of the PCR is the need for two primers which are complementary to the 5' and 3' ends of the target nucleic acid which is to be amplified. Not only must the primers be made complementary to two known and non-contiguous portions of the target nucleic acid, the primers must be oriented such that their 3' extension products proceed toward each other. If the sequences at both ends of the segment to be amplified are not known, complementary primers cannot be synthesized and the standard PCR protocol cannot be performed.

The object of the present invention is to overcome the need for sequence information at both ends of the segment to be amplified. In short, the present invention comprises a method which enables the PCR to be performed when sequence information is known for only a single region of the target Nucleic acid. The invention also provides a method for contiguously amplifying and sequencing a very long nucleic acid region without having to sub-clone the nucleic acid to arrive at nucleic acid targets of smaller size.

SUMMARY OF THE INVENTION

The invention is drawn to a method of specifically amplifying a selected region of nucleic acid (DNA or RNA). The method comprises first annealing a 5'-blocked oligonucleotide primer to a target nucleic acid molecule. The target nucleic acid molcule has a region of known nucleotide sequence and a region of unknown nucleotide sequence 3' to the known nucleotide sequence. The sequence to be selectively amplified is the region of unknown nucleotide sequence. The oligonucleotide primer is designed to anneal to the region of known nucleotide sequence.

The 5'-blocked oligonucleotide primer, now annealed to the known region of the target nucleic acid, is then extended in the 3' direction to yield a DNA strand complementary to at least a portion of the region of unknown nucleotide sequence in the target nucleic acid molecule.

The complementary nucleic acid strand so synthesized is then coupled at its 3' terminus to a 3'-blocked oligonucleotide of known identity, thereby yielding a nucleic acid fragment of known sequence at its 5' and 3' termini. The nucleic acid fragment so formed, which has a known sequence at is 5' and 3' terminus is then amplified using conventional means, preferably using the PCR.

The primary advantage of the present invention is that it enables the specific amplification of long stretches of DNA or RNA of unknown nucleotide sequence when only a single region of the target DNA or RNA is of known sequence. More specifically, the invention enables specific PCR amplification of a region of DNA or RNA of unknown sequence which lies 3' to a region of known sequence, using only a single primer of known sequence.

A host of other advantages become immediately apparent in view of the ability to amplify specifically target nucleic acid of unknown sequence using only a single primer. Most readily apparent is that the method can be used to amplify reiteratively a first (initially) unknown region of DNA or RNA, sequence the unknown region, and then use the newly-generated sequence information to amplify a second (initially) unknown region of DNA or RNA which is contiguous to the first region, and so on, ad infinitum.

This aspect of the invention is tremendously advantageous for sequencing very long nucleic acid molecules using the PCR procedure because it requires only limited sequence information for the target nucleic acid. Moreover, the information generated in each cycle of the process enables contiguous regions of nucleic acid of unknown sequence to be successively amplified (specifically) and then sequenced (or manipulated by any other means, such as by restriction digestion, cloning, etc.). Using the present invention, the starting knowledge one needs to possess is simply the nucleotide sequence of a single, very small region of target DNA or RNA. The method described herein can then be used to amplify, in contiguous fashion, very long regions of DNA or RNA of unknown sequence, such as undigested genomic DNA, without the need for sub-cloning it into smaller fragments. By sequencing the amplified product, the process can by applied reiteratively to elucidate the sequence of vast stretches of previously unsequenced DNA or RNA.

Another advantage of the invention is that, like convetional PCR, it is readily automatable. Automatable oligonucleotide synthesizers are now widely available commercially, as are automatable PCR cycling blocks and automatable DNA sequencing machines. For example, such machines are available in the United States from Perkin-Elmer Corporation, Foster, Calif.; Beckman Instruments, Columbia, Md., and others. Because the process can be performed reiteratively, it is extremely well-suited to automation using existing equipment. After generating the first 5'-blocked primer, the annealing, initial amplifying, coupling of a 3' terminus, and subsequent amplifying and sequencing of the target DNA are all automatable using existing equipment. Knowledge gained from each successive cycle can be used to generate (automatically) a new 5'-blocked primer for use in the next cycle.

Further aims, objects, and advantages of the amplification method will become apparent upon a complete reading of the Detailed Description which follows.

DETAILED DESCRIPTION OF THE INVENTION

As noted above, the present invention is a method which enables the selective amplification of a target nucleic acid molecule, having only the knowledge enough of the nucleotide sequence of the target molecule to fabricate one oligonucleotide primer. For purposes of brevity only, the discussion which follows refers only to DNA. The process can, however, be applied with equal success to RNA.

The first step of the process is to fabricate an oligonucleotide primer which is complementary in sequence to a region of known sequence in the target DNA. The primer is then chemically blocked at its 5' terminus to prohibit any further chemical or enzymatic reactions at the 5' terminus of the primer. The primer is referred to in the rest of the description and claims as the 5'-blocked oligonucleotide primer, or simply the 5'-blocked primer.

Figure 1A:
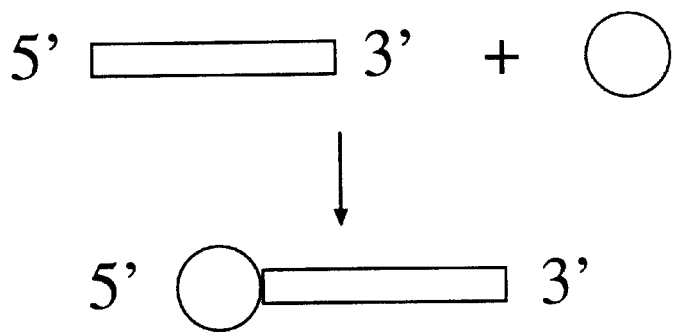
FIG. 1A is a schematic representation of the synthesis of a 5'-blocked oligonucleotide primer.

Oligonucleotide synthesis is exceedingly well known in the field and will not be described in further detail herein. Numerous national companies provide custom oligonucleotide synthesis. Blocking the primer at its 5' terminus is also accomplished using various chemical means, several types of which are described in greater detail hereinbelow. A schematic of the formation of a 5'-blocked primer is shown in FIG. 1A.

The 5'-blocked primer is then annealed (under standard hybridization conditions) to the region of known nucleotide sequence on the target DNA. For an exhaustive treatment of standard DNA techniques such as annealing, melting, PCR, etc. see Sambrook, J.; Fritsch, E. F.; Maniatis, T. (1989), *Molecular Cloning: A Laboratory Manual;* Cold Spring Harbor Laboratory Press: New York, N.Y.

Figure 2:
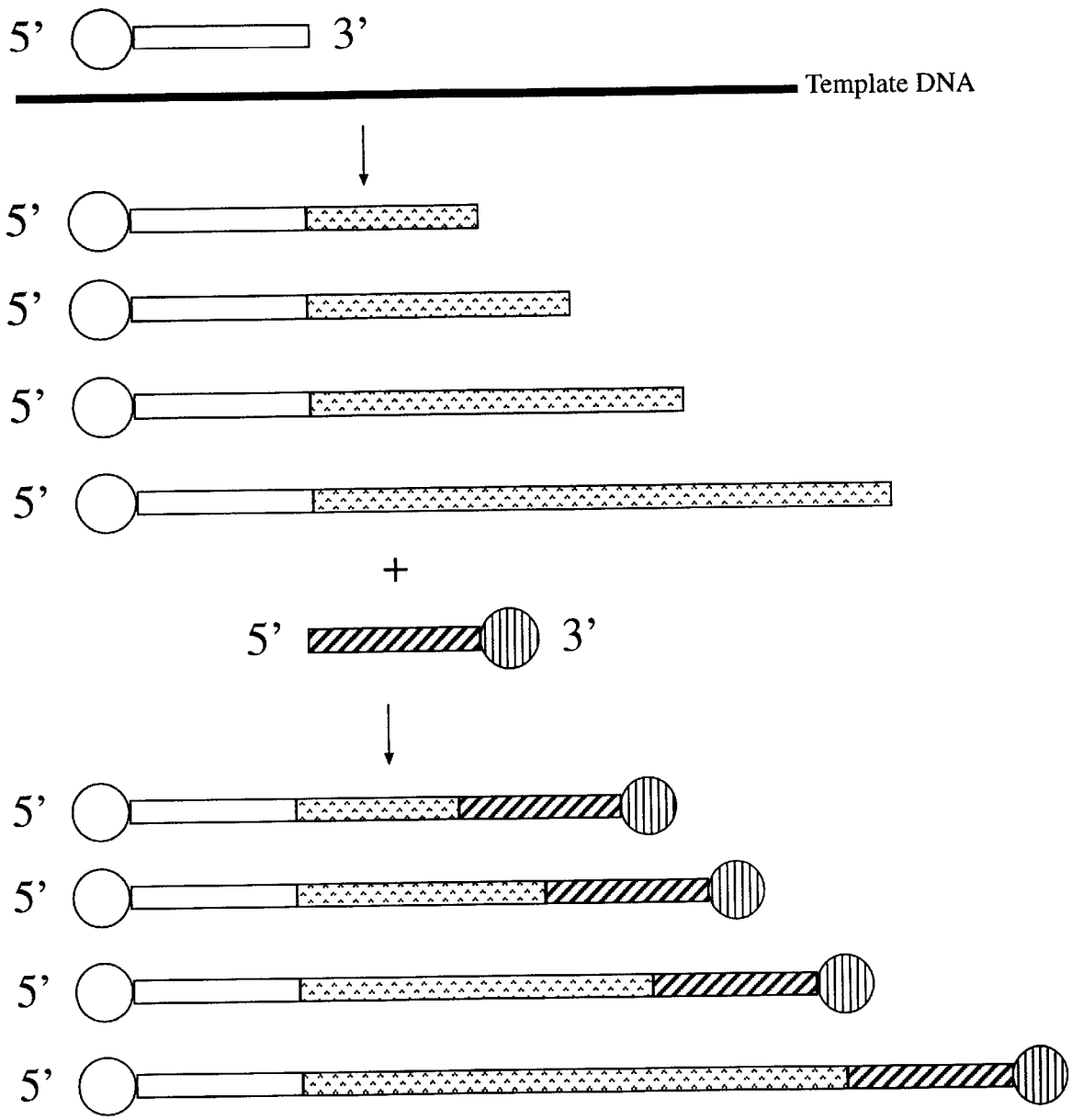
FIG. 2 is a schematic representation of annealing a 5'-blocked primer to a target DNA molecule at a region of known nucleotide sequence on the target DNA, extending the primer to form a DNA strand complementary to at least a portion of the region of unknown nucleotide sequence of the target DNA, and then coupling complementary DNA strand so formed to a 3'-blocked oligonucleotide of known sequence, thereby yielding a DNA fragment having a known sequence at its 5' and 3' termini and a region of unknown sequence therebetween.
Figure 3:
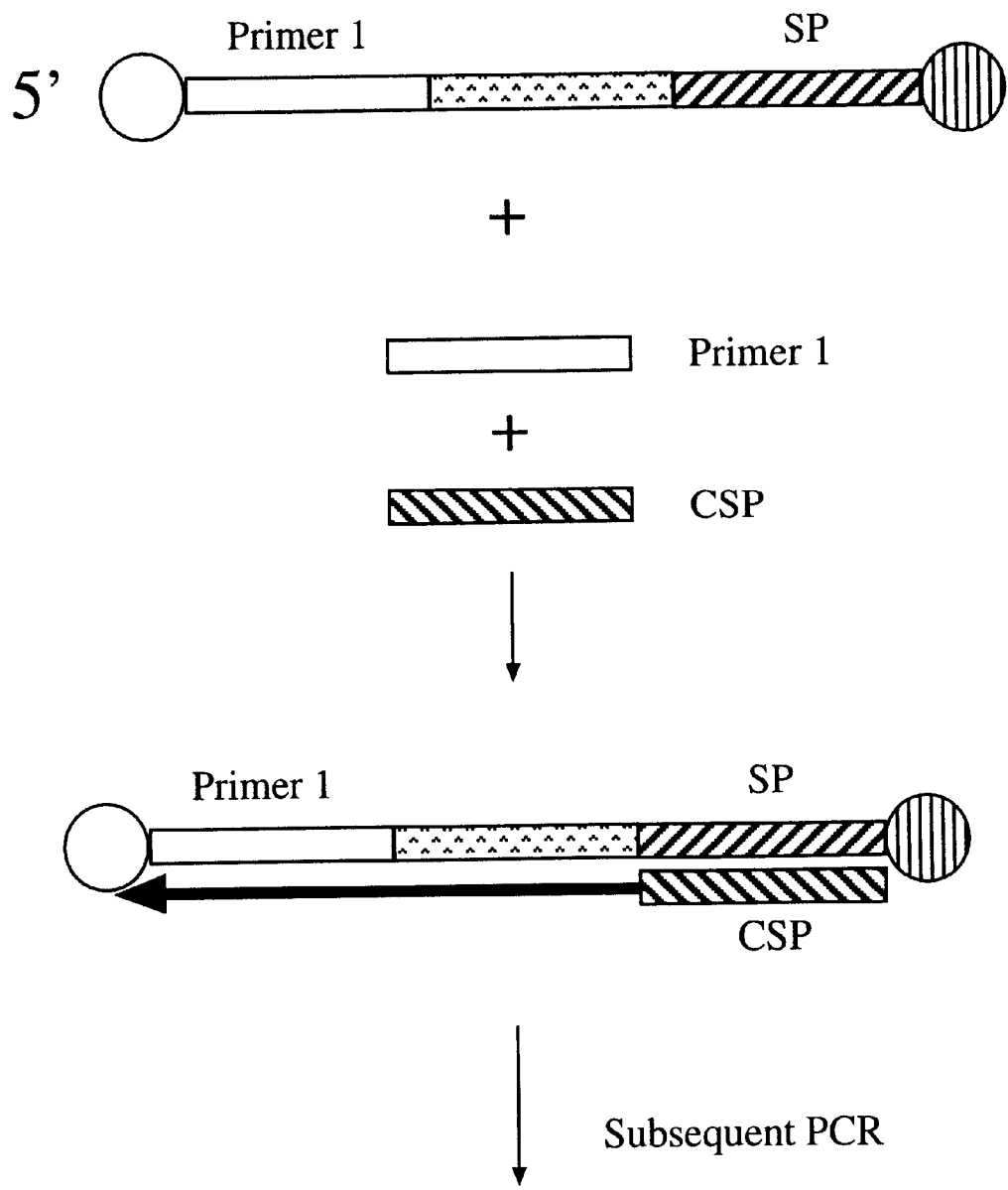
FIG. 3 is a schematic representation of the PCR performed on the DNA fragment formed in FIG. 2.

The 5'-blocked primer, now annealed to the region of known sequence in the target DNA, is extended in the 3' direction using a DNA polymerase, preferably a thermostable polymerase, and most preferably Taq DNA polymerase. The annealing and extension steps are shown schematically in the top portion of FIG. 2. As shown in FIG. 2, the extension products may be of various lengths and encompass smaller or larger regions of the area of unknown nucleotide sequence on the target DNA.

The annealled and extended products are converted into single-stranded DNA molecules, preferably by "melting" the DNA strands. This yields a collection of single-stranded DNA molecules as shown in the top portion of FIG. 2. Each single-stranded DNA molecule has a blocked 5' terminus, a known 5' terminal sequence, and a region of unknown DNA sequence. The 3' ends of all these molecules contain a free and reactive 3'-OH group.

Figure 1B:
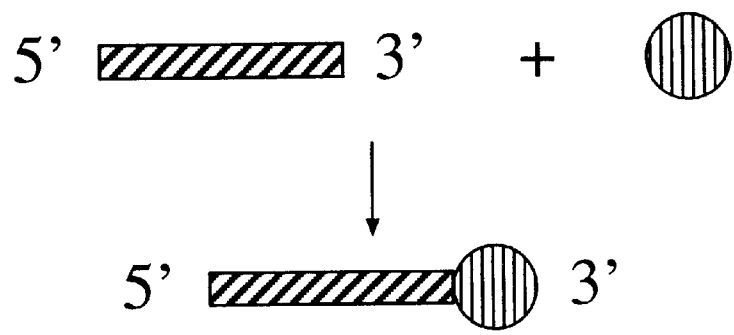
FIG. 1B is a schematic representation of the synthesis of a 3'-blocked oligonucleotide primer.
Figure 1C:
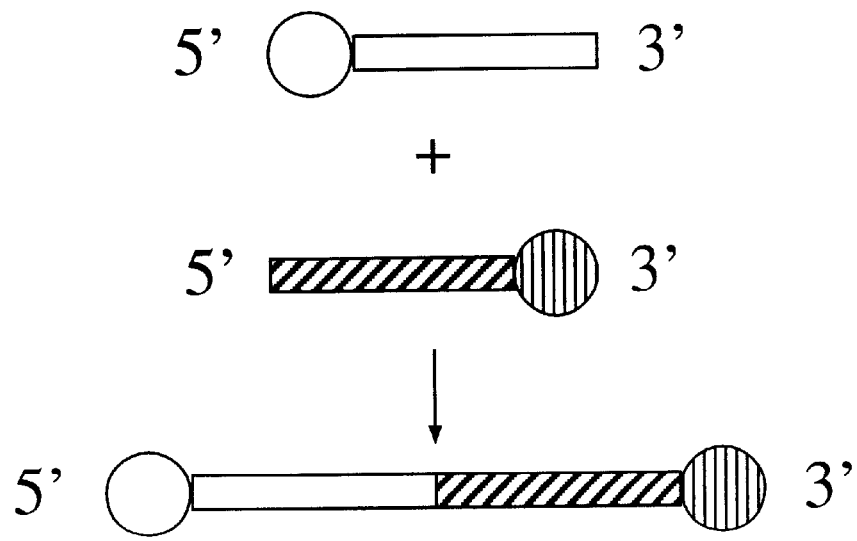
FIG. 1C is a schematic representation of the coupling of a 5'-blocked primer and a 3' blocked primer.

A 3'-blocked oligonucleotide of arbitrary but known sequence is then coupled to the 3' end of the extension products. Like the 5'-blocked primer, the 3'-blocked oligonucleotide is prevented from further chemical or enzymatic reaction at its 3' terminus. It does, however, have a free and potentially reactive 5'-OH group Blocking the oligonucleotide at its 3' terminus is also accomplished using various chemical means, several types of which are described in greater detail below. A schematic of the formation of a 3'-blocked primer is shown in FIG. 1B.

The reactive 5'-OH end of the 3'-blocked oligonucleotide is then coupled to the reactive 3'-OH end of the 5'-blocked extension product described above to yield a population of DNA molecules as shown in the bottom portion of FIG. 2. Each of these molecules is blocked at its 5' and 3' termini, has a known sequence at its 5' and 3' termini, and a region of unknown nucleotide sequence diposed between the 5' and 3' known region.

The coupling of the 3'-blocked oligonucleotide to the 5'-blocked extension products can be accomplished by chemical or enzymatic means for linking nucleotide bases in the physiologically-correct 5' to 3' orientation. By using the blocking procedure, the proper orientation of the coupling of the 3'-blocked oligonucleotide to the 5'-blocked extension products is ensured. Without the blocking procedure, the arbitrary olignucleotide could couple also to the 5' end of the extension products.

Because these molecules now include a region of unknown nucleotide sequence flanked between two regions of known nucleotide sequence, the unknown regions can be specifically amplified with the PCR, using primers which are complementary to the known 5' and 3' terminal sequences.

In the first round of PCR, a primer complementary in sequence to the 3'-blocked oligonucleotide is used to generate a double-stranded template for the subsequent cycles of the PCR. Then, by adding primers complementary to both the 5'-blocked primer and 3'-blocked oligonucleotide, the PCR will function in its normal fashion.

To optimize the process, it is preferred that the 5'-blocked primer be designed such that its sequence yields a Tm substantially similar to the Tm of the 3'-blocked arbitrary primer. By optimizing the Tm of the two oligonucleotides, the subsequent PCR will provide maximum yield.

All of the amplified DNA molecules start at the 5'-blocked primer site on the template DNA and end at variable distances from the 5'-blocked primer, at the point where the 3'- blocked oligonucleotide has been coupled.

The amplified DNA can be sequenced from the first primer binding site by primer walking (cycle sequencing), in known fashion, or by any other means now known or developed in the future for the sequencing of nucleic acids. Although the amplified DNA molecules end at variable lengths from the 5'-blocked primer location, conventional sequencing techniques yield readable sequence data until the end of the longest fragment.

Using the above steps, the invention can also be used to specifically amplify great lengths of DNA of mostly unknown sequence using the conditions for the Long PCR. In this process, a long single-stranded DNA (up to perhaps 10 kilobases or even more), is synthesized from a known first primer site using the above-described protocol. A 3'-blocked oligonucleotide is added at the 3' end of the long single-stranded DNA, and the DNA is amplified by using PCR conditions appropriate for long DNA amplification.

While the resultant amplified DNA may end at variable lengths, the use of partly fixed primers with variable numbers of fixed sequences (5, 6, 7, or more fixed bases) (the subject of approved patent application Ser. No. 08/406,545 to Periannan Senapathy) will generate one or a very small number of discrete DNA fragments, all of which start from the 5'-blocked primer. This DNA can then be sequenced using any means now known or developed in the future. By using primers with appropriately longer fixed bases and stringent PCR conditions, shorter amplification products can be avoided.

There are many methods to block a DNA oligonucleotide at its 5' end or its 3' end. This can be achieved by modifying the 5'-OH or the 3'-OH end of the DNA oligonucleotide. Typically a phosphate group, a phosphate ester, or using an inverted 3'–3' linkage is utilized. However, side reactions during deprotection of the oligonucleotide or enzymatic impurities may free the 3' hydroxyl group to a small extent, but the fraction is so little that it will not affect the purpose of a specific blocking. An effective way to block the 3' end of the DNA is to use the 3-propyl phosphate formed with 3' spacers containing a 3' carbon chain.

The methods to block the 5'-OH end of the DNA are similar to blocking the 3' end. An easy method to use is the 5'-Ome-dT, which essentially leaves the DNA without a 5'-OH. This can also be achieved by a number of different DNA labels (special dyes or linkers attached to the 5' end) which leaves the 5' end without a hydroxyl group.

The additions of blockers to the 3' or the 5' end of a DNA can easily be done during the synthesis of the DNA in the laboratory. For the 3' blocking of a synthetic DNA, special columns can be used during the synthesis of the DNA or it can be chemically modified after the synthesis. The 5' end is usually modified with special "bases" during synthesis and sometimes with chemical or enzymatic modification after the synthesis.

Depending on use, some blockers are more effective than others. Some polymerases have exonuclease activity for proofreading. Non-nucleosidic spacers and modifiers at the 3' or 5' ends do not as effectively terminate the sequence as a 5' or 3'-phosphate ester which is phosphatase and nuclease resistant. Using 5'phosphoramidites or 5'supports yields 5'—5' or 3'—3' linkages, which are also nuclease resistant.

Block the 3' terminus of an oligonucleotide from allowing polymerase extension may be achieved by modifying the 3' terminus with a phosphate group, a phosphate ester, or using an inverted 3'—3' linkage. However, side reactions during deprotection of the oligonucleotide or enzymatic impurities may free the 3' hydroxyl group to a small extent. The 3'-propyl phosphate formed using 3' spacers with a 3' carbon chain is a simple and effective non-nucleoside blocker of the 3' terminus.

An effective way for blocking the 3' terminus is to use a 2',3' dideoxynucleoside support. However, this is available for a limited number of bases.

In situations where it is necessary to have a selection of all four bases available, it is possible to use 3'-deoxynucleoside supports as 3' terminators. Although the 2' hydroxyl group is still present in the final oligonucleotides, it is not a substrate for the routinely used polymerases.

Various agents can be used to block either the 5' or 3' terminus of a nucleic acid molecule. The list which follows is non-exclusive, and other agents now known or developed in the future to prevent the enzymatic extension of nucleic acids by polymerases can be used.

Chemical Phosphorylation Agents

2-{2-(4.4'-Dimethoxytrityloxy)-ethylsulfonyl}ethyl-(2-cyanoethyl)-(N,N,-diisopropyl)-phosphoramidite)

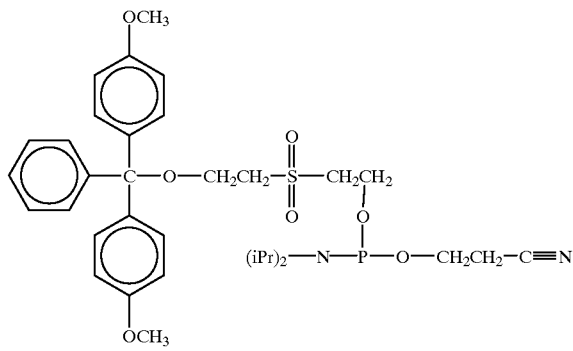

3-{(4,4'-Dimethoxytrityloxy)-2,2-dicarboxyethyl}propyl-(2-cyanoethyl)-(N,N-diisopropyl)-phosphoramidite

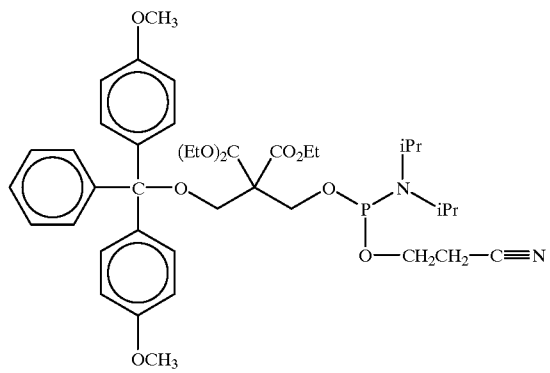

Chemical Phosphoramidite on Support

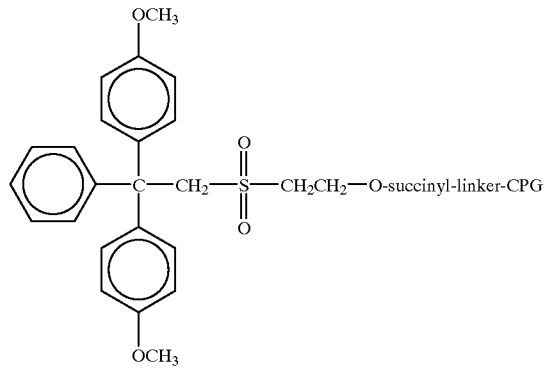

CPG=Control Pore Glass
linker=any suitable linker, such as a long chain alkylamino linker The control pore glass is the non-reactive support used in the synthesis column. The linked moiety is then the primary base used in the synthesis of a blocked oligonuceotide strand. When the dimethoxytrityl moiety is hydrolyzed, it generates a free-OH group, which enables the continuation of the synthesis by further addition of a nucleotide.

Spacer Phosphoramidite C3

3-O-Dimethoxytrityl-propyl-1-{(2-cyanoethyl)-N,N-diisopropyl)}phosphoramidite

Spacer C3-Support

1-Dimethoxytrityloxy-propanediol-3-succinyl)-linker-CPG

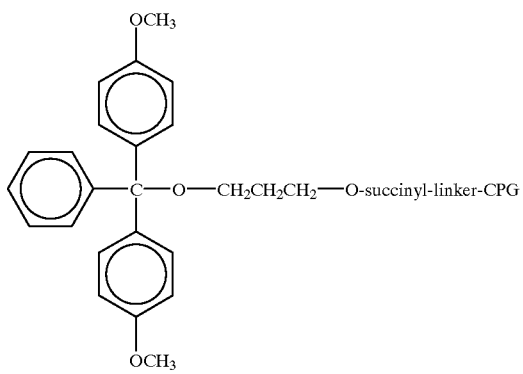

Additionally a 9-carbon chain can be used as a product for preparing an oligonucleotide with a 3'-terminus blocked with a triethyleneglycol group to block polymerase extension with a mixed polarity polyether.

2,3'-dideoxynucleoside

5'Dimethoxytrityl-N-succinoyl-CPG,2,3'deoxyadenosine

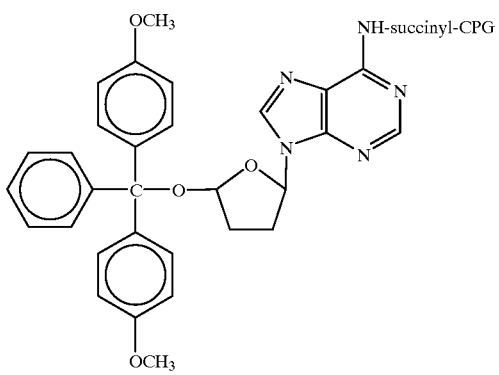

3'-deoxynucleosides

5'-Dimethoxytrityl-N-benzoyl-3'-deoxycytosine,2'-succinoyl-linker-CPG

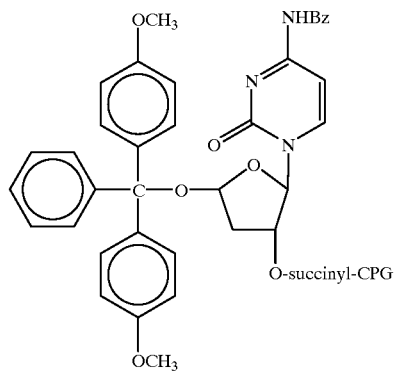

In situations where ligation must be blocked at the 5' terminus, 5'-OMe-dT may be used. Additionally any 5' label can be utilized as a blocker to ligation. Any base, minor base, or label that can be synthetically added to the 5' terminus of the oligonucleotide that blocks or does not contain the 5' hydroxyl will act as 5' blocker.

5'-OMe-dT

5'-O-methyl-2'deoxythymidine, 3'-{(2-cyanoethyl)-(N,N-diisopropyl)}-phosphoramidite

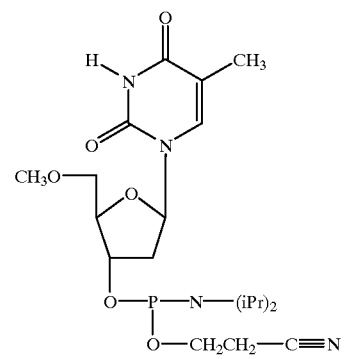

Biotin Phosphoramidite

1-N-(4,4'-Dimethoxytrityl)-biotinyl-6-aminohexyl}-2-cyanoethyl-(N,N-diisopropyl)-phosphoramidite

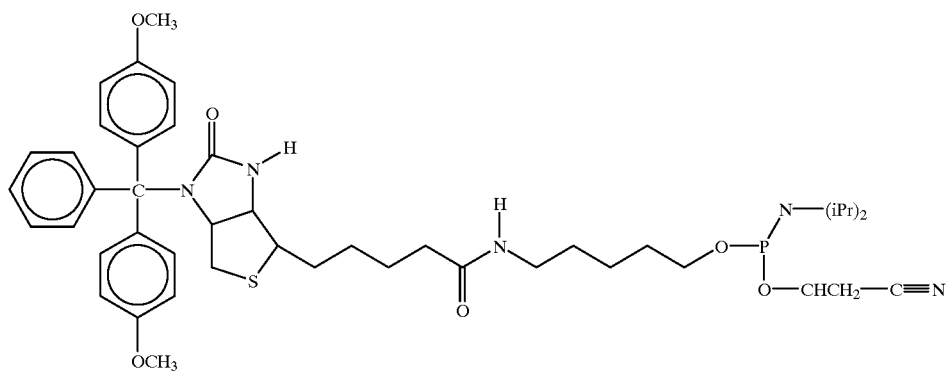

It is simple to block the 5' terminus using 5'-OMe-T or the 3' terminus with 2',3'-dideoxy-or 3'-deoxynucleosides. However, some polymerases use exonuclease activity for proof reading. Any non-nucleosidic group at the 3' or 5' termini, spacers, and/or modifiers, effectively terminate the sequence as a 5' or 3'-phosphate ester which is phosphatase and nuclease resistant. Using 5'-phosphoramidites or 5'supports makes 5'—5' or 3'—3' linkages, which are also nuclease resistant.

The invention is not limited to the particular reagents, protocols, etc. described hereinabove, but includes all modified and equivalent forms thereof which are within the scope of the following claims.

What is claimed is:

1. A method of specifically amplifying a selected region of nucleic acid comprising:
   (a) annealing an oligonucleotide primer that is chemically modified at its 5' terminus to prohibit further chemical or enzymatic reactions from occurring at the 5' terminus of the primer, said primer being designated the 5'-blocked primer to a target nucleic acid molecule having a region of known nucleotide sequence and a region of unknown nucleotide sequence 3' to the known nucleotide sequence, wherein the oligonucleotide primer anneals to the region of known nucleotide sequence; then
   (b) extending the 5'-blocked primer in the 3' direction to yield a nucleic acid strand complementary to at least a portion of the region of unknown nucleotide sequence in the target nucleic acid molecule, then
   (c) coupling to the complementary nucleic acid strand of step (b) at its 3' terminus an oligonucleotide of known sequence that is chemically modified at its 3' terminus to prohibit further chemical or enzymatic reactions from occurring at the 3' terminus of the oligonucleotide, said oligonucleotide being designated the 3'-blocked oligonucleotide, to yield a nucleic acid fragment of known sequence at its 5' and 3' termini; and then
   (d) amplifying the nucleic acid fragment of step (c).

2. The method of claim 1, wherein DNA is amplified.

3. The method of claim 1, wherein RNA is amplified.

4. The method of claim 1, wherein in steps (a) and (c), the 5'-blocked oligonucleotide primer and the 3'-blocked oligonucleotide are blocked at their respective 5' and 3' termini by a moiety independently selected from the group consisting of a phosphate, a phosphate ester, a phosphoramidite, a 3'—3'- or 5'–5'-oriented nucleotide, an alkyl phosphate, a modified nucleotide base, a 3'-deoxynucleotide, and a 2',3'-dideoxynucleotide.

5. The method of claim 1, wherein in step (d), the nucleic acid fragment is amplified by polymerase chain reaction.

6. The method of claim 1, wherein in step (b) the oligonucleotide is extended using a thermostable nucleic acid polymerase.

7. The method of claim 1, wherein in step (b) the oligonucleotide is extended using Taq DNA polymerase.

8. The method of claim 1, further comprising the step of e) sequencing the amplified nucleic acid fragment of step d).

9. A method of specifically amplifying a selected region of DNA comprising:
   (a) annealing an oligonucleotide primer that is chemically modified at its 5' terminus to prohibit further chemical or enzymatic reactions from occurring at the 5' terminus of the primer, said primer being designated the 5'-blocked primer to a target DNA molecule having a region of known nucleotide sequence and a region of unknown nucleotide sequence 3' to the known nucleotide sequence, wherein the oligonucleotide primer anneals to the region of known nucleotide sequence; then
   (b) extending the oligonucleotide primer in the 3' direction to yield a DNA strand complementary to at least a portion of the region of unknown nucleotide sequence in the target DNA molecule; then
   (c) coupling to the complementary DNA strand of step (b) at its 3' terminus an oligonucleotide of known sequence that is chemically modified at its 3' terminus to prohibit further chemical or enzymatic reactions from occurring at the 3' terminus of the oligonucleotide, said oligonucleotide being designated the 3'-blocked oligonucleotide, to yield a DNA fragment of known sequence at its 5' and 3' termini; and then
   (d) amplifying the DNA fragment of step (c) using polymerase chain reaction.

10. The method of claim 9, wherein in step (b) the oligonucleotide is extended using a thermostable DNA polymerase.

11. The method of claim 9, wherein in step (b) the oligonucleotide is extended using Taq DNA polymerase.

12. The method of claim 9, further comprising the step of e) sequencing the amplified DNA fragment of step d).

* * * * *